United States Patent
Lee

(10) Patent No.: US 11,026,382 B2
(45) Date of Patent: Jun. 8, 2021

(54) **PRODUCING METHOD OF *CANNABIS SATIVA* L. SEED**

(71) Applicant: FAMENITY CO., LTD., Gwacheon-si (KR)

(72) Inventor: Ji Won Lee, Gwacheon-si (KR)

(73) Assignee: FAMENITY CO., LTD., Gwacheon-si (KR)

( * ) Notice: Subject to any disclaimer, the term of this patent is extended or adjusted under 35 U.S.C. 154(b) by 14 days.

(21) Appl. No.: 16/458,248

(22) Filed: Jul. 1, 2019

(65) Prior Publication Data

US 2021/0000029 A1 Jan. 7, 2021

(51) Int. Cl.

| | |
|---|---|
| *A01G 7/04* | (2006.01) |
| *A01H 3/02* | (2006.01) |
| *A01H 5/10* | (2018.01) |
| *A01H 1/02* | (2006.01) |
| *A01H 6/28* | (2018.01) |
| *A01H 3/04* | (2006.01) |
| *A01G 22/00* | (2018.01) |

(52) U.S. Cl.
CPC .............. *A01H 3/02* (2013.01); *A01G 7/045* (2013.01); *A01G 22/00* (2018.02); *A01H 1/02* (2013.01); *A01H 3/04* (2013.01); *A01H 5/10* (2013.01); *A01H 6/28* (2018.05)

(58) Field of Classification Search
CPC .......... A01G 7/00; A01G 22/00; A01G 7/045; A01D 91/00; A01C 14/00; A01H 4/055; A01H 6/28; A01H 3/02; A01H 3/04; A01H 3/00; A01H 5/10; A01H 1/02
See application file for complete search history.

(56) References Cited

U.S. PATENT DOCUMENTS

| | | | | |
|---|---|---|---|---|
| 9,737,077 B2 * | 8/2017 | Momma | .................. | A01H 3/04 |
| 2015/0274606 A1 * | 10/2015 | Helskens | ................. | C05D 9/00 71/62 |

FOREIGN PATENT DOCUMENTS

WO WO2009125198 A2 10/2009

OTHER PUBLICATIONS

Allen Dr. Allen's 16 hour dark photoperiod 2016 Cannabis Digest, retrieved on Aug. 3, 2020, retrieved from the Internet at https://cannabisdigest.ca/dr-allens-16-hour-dark-photoperiod/, 8 pp. (Year: 2016).*
Civantos. Preparing for the Outdoor Cannabis Cultivation Season, 2017, retrieved on Aug. 18, 2020, retrieved from the Internet https://www.dinafem.org/en/blog/preparing-season-crop-cannabis-marijuana-outdoor/, 10 pp. (Year: 2017).*
Hennings. How to Use Liquid Nutrients for Cannabis Plants, 2018, retrieved on Aug. 18, 2020, retrieved from the Internet at https://www.dinafem.org/en/blog/preparing-season-crop-cannabis-marijuana-outdoor/, 6 pp. (Year: 2018).*
Hopper et al. Crop Growth Requirement, Plant growth chamber handbook North Central Regional Research, retrieved on Aug. 18, 2020, retrieved from the Internet at https://www.dinafem.org/en/blog/preparing-season-crop-cannabis-marijuana-outdoor/, 1997, 217-225. (Year: 1997).*
Pot Pan Kitchen. Behind the Scenes: Hemp Farming for CBD 2019, retrieved on Aug. 18, 2020, retrieved from the Internet at https://pot-pan-kitchen.myshopify.com/blogs/news/behind-the-scenes-hemp-farming-for-cbd, 7pp. (Year: 2019).*
Ram et al. Induction of Fertile Male Flowers in Genetically Female Cannabis sativa Plants by Silver Nitrate and Silver Thiosulphate Anionic Complex, Theor. Appl.Genet. 62,369-375, 1982 (Year: 1982).*

* cited by examiner

*Primary Examiner* — June Hwu
(74) *Attorney, Agent, or Firm* — STIP Law Group, LLC

(57) ABSTRACT

The present invention relates to a method for producing *Cannabis sativa* L. seed, and more particularly, to a method for producing *Cannabis sativa* L. seed for efficiently cultivating a low-narcotic *Cannabis* variety, and when *Cannabis sativa* L. seeds produced by the production method are used, it is possible to cultivate *Cannabis* female plants where female flowers are formed, and it is possible to improve the quantity of *Cannabis* female flowers. Further, when a *Cannabis* extract is prepared using the *Cannabis* female flowers, it is possible to prepare a low-narcotic *Cannabis* extract.

6 Claims, No Drawings

PRODUCING METHOD OF *CANNABIS SATIVA* L. SEED

TECHNICAL FIELD

The present invention relates to a method for producing *Cannabis sativa* L. seed, and more particularly, to a method for producing *Cannabis sativa* L. seed, capable of producing *Cannabis sativa* L. seed grown in *cannabis* female plants.

BACKGROUND ART

*Cannabis sativa* L. is generally designated as an illegal drug called *cannabis* or marijuana, so that the use thereof has been prohibited in many countries.

Recently, as *Cannabis sativa* L. has been legalized in some countries, major interests have been focused on *cannabis* ingredients.

*Cannabis* is made to be smoked in the form of tobacco cigarettes by drying leaf and flower parts of hemp, contains a hallucination ingredient called THC, and thus is classified as a pharmacological hallucinogen. *Cannabis sativa* L. is also classified as flax or hemp, and has long been used as a medicinal material or a euphoriant.

In particular, those obtained from female plant flower spikes and leaves of cultivated hemp are called ganja, and those obtained from wild hemp are called as marijuana or bhang. The term marijuana is derived from Marihuango which means "intoxicated" in Portuguese.

*Cannabis sativa* L. has both excitatory and inhibitory actions, but is generally classified as a hallucinogen. When a small amount of *Cannabis sativa* L. is smoked, an effect of a mild stimulant appears, and when a large amount of *Cannabis sativa* L. is smoked, effects of feeling of floating in the air, a rapid change in emotion, illusion and hallucination appear, and when an extremely large amount of *Cannabis sativa* L. is smoked, a state of insanity is also caused due to addiction.

People who smoke *cannabis* emit smell like grass and smoke from clothes and body thereof, are more talkative or a bit more excited than the inherent personality in terms of behavior, and sometimes exhibit absent-minded state or depression, and ataxia (symptom in which a constant movement cannot be made due to the harmony disorder between each muscle even though there is no muscle disorder) phenomena.

It is known that major ingredients of *Cannabis sativa* L. consist of various ingredients such as tetrahydrocannabinolic acid (THCa), cannabidiolic acid (CBDa), cannabinolic acid (CBNa), cannabichromenic acid (CBCa), cannabinol (CBN), cannabidiol (CBD), and cannabichromene (CBC) in addition to aforementioned THC.

The World Health Organization (WHO) released a report revealing that cannabidiol (CBD) oil, which is made from *cannabis* extract, has efficacy for electro-cerebral disorder (epilepsy), Alzheimer's disease (dementia) and the like.

The World Anti-Doping Agency excluded CBD from prohibited drugs this year while publishing '2018 International Standard for Prohibited List'. CBD is a drug widely used by athletes for the purpose of treating pain, other materials which may be obtained from *cannabis*, such as hashish and marijuana, have been prohibited from being used, but CBD oil used for medical purposes was permitted.

As the pharmaceutical effect of CBD oil which uses *cannabis* extract as a raw material has been recognized as described above, there is a need for studies on a method for cultivating low-narcotic *cannabis* capable of efficiently preparing CBD oil.

PRIOR ART DOCUMENT

Patent Document (Patent Document 1) WO2009/125198 A.

SUMMARY OF THE INVENTION

The present invention has been made in an effort to provide a method for producing *Cannabis sativa* L. seed.

The present invention has also been made in an effort to provide a method for producing *Cannabis sativa* L. seed for the preparation of a low-narcotic *cannabis* extract.

The present invention has also been made in an effort to provide a method for producing *Cannabis sativa* L. seed that may grow *cannabis* female plants where female flowers bloom when *Cannabis sativa* L. seeds are sown and cultivated.

The present invention has also been made in an effort to provide a method for producing *Cannabis sativa* L. seed capable of being cultivated into *cannabis* female plants using low-narcotic *cannabis* seeds and preparing a low-narcotic *cannabis* extract using female flowers collected from the cultivated *cannabis* female plants.

An exemplary embodiment of the present invention provides a method for producing *Cannabis sativa* L. seed according to an exemplary embodiment of the present invention is a method for producing *Cannabis sativa* L. seed capable of cultivating *cannabis* female plants, and may include: spraying a first fertilizer composition on soil before sowing *Cannabis sativa* L. seeds; sowing *Cannabis sativa* L. seeds after tilling and preparing the soil on which the first fertilizer composition is sprayed; inducing the formation of budding flowers by providing *Cannabis sativa* L. germinated from the *Cannabis sativa* L. seeds with light for 10 to 12 hours; inducing the formation of male flowers in *cannabis* female plants by removing all *Cannabis sativa* L. where male budding flowers are formed and spraying a second fertilizer composition on *Cannabis sativa* L. where female budding flowers are formed, among *Cannabis sativa* L. where the budding flowers are formed; and producing seeds by fertilizing pollen in the male flowers formed in the *cannabis* female plants with female flowers.

The first fertilizer composition may include a nitrogen fertilizer, a phosphate fertilizer, a potassium fertilizer, and porous silica.

The second fertilizer composition includes a nitrogen fertilizer, a phosphate fertilizer, a potassium fertilizer, and porous silica, and the porous silica is a product in which a mixture of aminoethoxyvinyl glycine (AVG), α-aminoisobutyric acid (AIB), and an aqueous silver chloride (AgCl) solution is adsorbed.

The inducing of the formation of budding flowers includes providing light under a photosynthetic photon flux density (PPFD) condition of 15 to 20 $\mu Mm^{-2}s^{-1}$ for 15 to 30 days; and then providing light under a photosynthetic photon flux density (PPFD) condition of 30 to 40 $\mu Mm^{-2}s^{-1}$ for 15 to 30 days.

The female flowers are used as a *cannabis* extract by harvesting flowers and flower petals, and the *cannabis* extract is low narcotic.

The low narcotic may include tetrahydrocannabinol (THC) in an amount of 0.5 wt % or less in the ingredients of the total extract.

The low narcotic may include cannabidiol (CBD) in an amount of 0.5 wt % or more in the ingredients of the total extract.

A method for producing *Cannabis sativa* L. seed according to another exemplary embodiment of the present invention may include: sowing *Cannabis sativa* L. seeds; providing *Cannabis sativa* L. germinated from the *Cannabis sativa* L. seeds with light under a photosynthetic photon flux density (PPFD) condition of 15 to 20 $\mu Mm^{-2}s^{-1}$ for 5 hours to 16 hours daily for 15 to 30 days; thereafter, providing light under a photosynthetic photon flux density (PPFD) condition of 30 to 40 $\mu Mm^{-2}s^{-1}$ for 5 hours to 16 hours daily for 15 to 30 days; treating a shoot apex of the *Cannabis sativa* L. where the female budding flowers are formed with an ethylene inhibitor; and producing seeds by inducing the formation of male flowers in *cannabis* female plants by the ethylene inhibitor, and pollinating the male flowers with female flowers in the female plant.

The ethylene inhibitor may be selected from the group consisting of aminoethoxyvinyl glycine (AVG), α-aminoisobutyric acid (AIB), an aqueous silver nitrate ($AgNO_3$) solution, an aqueous silver chloride (AgCl) solution, and a mixture thereof.

Hereinafter, the present invention will be described in more detail.

In the present invention, the "low narcotic" means that an extract is obtained from flowers and flower petals separated from cultivated *Cannabis sativa* L., tetrahydrocannabinol (THC) is included in an amount of 0.5 wt % or less, and cannabidiol (CBD) is included in an amount of 0.5 wt % or more, in the extract.

*Cannabis sativa* L. (*cannabis*, hemp), together with the *Humulus* geneus (hops), belongs to the family of Cannabinaceae, and, for example, does not include any cannabinoids. For the botanical and chemotaxonomical differentiation of the genus *Cannabis*, there are two different concepts.

One differentiates between three species, *Cannabis sativa* Linnaeus, *Cannabis* indica LAM, and *Cannabis ruderalis*, while a different theory only sees the existence of the one collective species *Cannabis sativa* L. made up of the subspecies *Cannabis sativa* ssp. *sativa* and ssp. indica.

The *cannabis* plant is differentiated into a drug type and a fiber type, with differentiation being performed on the basis of the content ratio of the main cannabinoids, cannabidiol (CBD), and tetrahydrocannabinol (THC).

Fiber hemp, whose cultivation is performed for fiber production, need not exceed a THC content of 0.3% relative to the dry plant mass, while the drug type may exhibit a THC content of about 5% to 15% relative to the dry plant mass.

The ratio of THC to CBD in fiber hemp is mostly 1.5. The content of THC is various, and thus may reach a ratio of 2:1 to 7:1.

*Cannabis sativa* L. occurs worldwide in all warm and moderate zones with the exception of the humid rainforests in the equatorial regions. *Cannabis sativa* L. is an annual to biennial, and an anemogamous plant may grow to a height of up to 8 m. The dioecious, rarely monoecious inflorescences include the active cannabinoids in the resin which is mostly secreted by the numerous glandular bracts in the leaf axils.

As a general rule, all the plant parts of *Cannabis sativa* L. with the exception of the seeds may contain cannabinoids.

The high cannabinoid concentrations are found in the floral bracts and fruit stalks.

The leaves have a low content of cannabinoids as a function of leaf age, while the stalk, particularly, the root exhibits clearly lower cannabinoid contents.

*Cannabis sativa* L. may exhibit a difference in cultivation methods depending on the use thereof. In the case of Korea, *Cannabis sativa* L. was usually cultivated so as to be used as fiber products. In this case, *Cannabis sativa* L. may be used as a fiber product by harvesting the stalk parts and peeling the stalk parts, or the inner leaf may be utilized as a material for construction materials and biodegradable plastics.

The seed and fruit are a sprout vegetable, a hemp seed, and a hemp seed oil, and may be used as a food material or a material for a cosmetic composition.

The unfertilized female flowers are used as a main material for a *cannabis* extract, and thus may be used to produce medicinal CBD oils.

Recently, the legalization of medicinal CBD oils has been promoted in many countries, and it has been confirmed that the CBD oils exhibit various efficacies.

Recently, CBD has been identified as the currently most advanced therapeutic agent for electro-cerebral disorder. Various clinical trials have proven that CBD is an effective therapeutic method for at least several types of electro-cerebral disorders, and EPIDIOLEX, which is pending FDA approval, are also undergoing three stages of clinical trials. Products containing CBD-based oils, supplements, gums, and highly concentrated extracts have already been used for the treatment of various diseases without a doctor's prescription. In fact, it is known that CBD may be used as a useful therapeutic agent for many other diseases such as Parkinson's disease, multiple sclerosis, neurogenic pain, depression, rheumatoid arthritis, and diabetic complications.

However, in order to extract the CBD, unfertilized female flowers of *Cannabis sativa* L. needs to be harvested, it is more important to include a large content of CBD in produced *Cannabis sativa* L., and a low-narcotic *Cannabis sativa* L. including a small THC content needs to be cultivated.

Thus, as the *Cannabis sativa* L. of the present invention, it is intended to use a variety having a THC content of 0.5 wt % or less and a CBD content of 0.5 wt % or more, such as IH3 or Cherry Wine.

The *cannabis* variety is not limited to the examples, pollen may be incorporated into varieties through seed growing between varieties to produce an F1 hybrid *cannabis* strain and harvest and use seeds thereof, but the present invention is not limited to the examples, and a low-narcotic *cannabis* variety can be used without limitation.

When cultivation is performed by using a low-narcotic *cannabis* variety, *Cannabis sativa* L. generally corresponds to a monoecious or dioecious plant.

Like ginkgo, a dioecious plant means that a tree with female flowers and a tree with male flowers are distinguished, and corresponds to poplar, Japanese yew, Japanese spice bush, and the like in addition to ginkgo.

A monoecious plant means a plant where all male and female flowers are blooming in the single plant, and is also referred to as monoecism. Pines and oriental white oaks correspond to the monoecious plant.

In addition to the dioecious or monoecious plants, a gynodioecious flower and a diclinous flower are also distinguished. The gynodioecious flower has pistils and stamens in one flower, whereas the diclinous flower is a flower that has only one of pistils and stamens, meaning a flower where female and male flowers bloom separately.

In the dioecious plants, only diclinous flowers are formed, and in the monoecious plants, gynodioecious flowers mostly bloom, but in some plants, diclinous flowers also bloom. In this case, *Cannabis sativa* L. is included in the plants where diclinous flowers exceptionally bloom among the monoecious plants.

*Cannabis sativa* L. may be monoecious or dioecious depending on the variety.

Even when *Cannabis sativa* L. corresponds to dioecism by the variety of *Cannabis sativa* L., diclinous flowers are formed unlike other dioecious plants, so that female flowers and male flowers may be differentiated.

The CBD ingredient of *Cannabis sativa* L. is known to be usually included in unfertilized female flowers, so that in order to extract highly productive CBD ingredients, the production of a seed capable of cultivating *cannabis* female plants which enables female flowers to be formed is inevitably needed.

Thus, the present invention intends to provide a method for producing *Cannabis sativa* L. capable of cultivating a *cannabis* female plant where female flowers are formed.

More specifically, the method is a method for producing *Cannabis sativa* L. seed capable of cultivating a *cannabis* female plant, and may include: spraying a first fertilizer composition on soil before sowing *Cannabis sativa* L. seeds; sowing *Cannabis sativa* L. seeds after tilling and preparing the soil on which the first fertilizer composition is sprayed; inducing the formation of budding flowers by providing *Cannabis sativa* L. germinated from the *Cannabis sativa* L. seeds with light for 10 to 12 hours; inducing the formation of male flowers in *cannabis* female plants by removing all *Cannabis sativa* L. where male budding flowers are formed and spraying a second fertilizer composition on *Cannabis sativa* L. where female budding flowers are formed, among *Cannabis sativa* L. where the budding flowers are formed; and producing seeds by fertilizing pollen in the male flowers formed in the *cannabis* female plants with female flowers.

As described above, as the *Cannabis sativa* L., a low-narcotic variety may be used, or it is possible to use an F1 hybrid seed where pollen is incorporated through seed growing of another variety different from the low-narcotic variety, but the *Cannabis sativa* L. is not limited to the variety.

*Cannabis sativa* L. may be cultivated in a glass greenhouse or a plastic greenhouse. In order to control the lighting conditions during cultivation, *Cannabis sativa* L. was cultivated in a glass greenhouse or a plastic greenhouse.

For the growth efficiency of *Cannabis sativa* L. and the efficient production of *Cannabis sativa* L. seeds, a mixture of a nitrogen fertilizer, a phosphate fertilizer, a potassium fertilizer, and porous silica may be used as a first fertilizer composition in soil before *Cannabis sativa* L. seeds are sowed.

As the first fertilizer composition, it is possible to use a mixed fertilizer obtained by mixing 30 to 50 parts by weight of the phosphate fertilizer, 30 to 50 parts by weight of the potassium fertilizer, and 40 to 60 parts by weight of porous fine powder silica based on 100 parts by weight of the nitrogen fertilizer.

With respect to the nitrogen fertilizer, the nitrogen fertilizer suitable for the growth of leaves is usually used at the early stage of crop growth, and ammonium sulfate, ammonium chloride, urea, lime nitrogen, ammonium nitrate and the like are representative. Among them, urea is converted into ammonium carbonate in the soil.

The phosphate fertilizer helps the growth of fruits, and examples of the phosphate fertilizer include superphosphate of lime (13,000 tons), fused phosphate fertilizer (78,000 tons), and the like. Since the main ingredient of these phosphate fertilizers is calcium phosphate monobasic [Ca(H$_2$PO$_4$)$_2$] and water-soluble, the effect of the fertilizer also appears early. Since phosphorus of the fused phosphate fertilizer is melted in a glass form along with silicic acid-.magnesium.calcium, and the like, the phosphorus is not dissolved well in water, but is gradually dissolved in soil, and then absorbed by plant bodies.

The potassium fertilizer may be effective for growth and root development and is mostly potassium chloride (KCl), and examples thereof also include potassium salts in addition to potassium sulfate (K$_2$SO$_4$). Since all the potassium fertilizers are water-soluble, the effect thereof appears early.

The porous silica is an inorganic particle and corresponds to a porous particle. Preferably, the porous silica is a porous silica impregnated with a natural extract and the natural extract is included in the pores of the porous silica, so that the growth of *Cannabis sativa* L. may be promoted by transferring an active ingredient of the natural extract in the soil.

The natural extract is an agar and glasswort extract.

The agar (*Gelidium amansii*) is a seaweed of the red algae plant Gelidiaceae, which is a plant that grows from May to November. The agar contains 10 to 20% of gelatin matter between interstices of somatic cells, so that agar-agar is made using the gelatin matter. Vegetable gelatin is produced by cleanly washing the agar with fresh water, boiling down those which is discolored by the sunshine, and filtering and cooling the remnants. A product made by freezing and drying the vegetable gelatin is agar-agar. Natural agar-agar has low purity, but high viscosity, whereas mechanically produced industrial agar-agar has high purity, but low viscosity. Agar-agar helps the peristaltic movement of the intestines, has low calories, and is in the spotlight on dieting, and is sometimes used to impart viscosity when ice cream and jam are made.

The scientific name of glasswort is named *Salicornia herbacea* or *Salicornia europaea*, which is used interchangeably. Glasswort contains 4 to 6% of salt contents, and thus exhibits a distinctive salty taste, and has been used to prepare vegetable salt and as a sub-ingredient for various foods. In particular, glasswort contains various minerals such as Na$^+$, K$^+$, Ca$^{2+}$, Mg$^{2+}$, Mn$^+$, and Zn$^{2+}$ abundantly while inhabiting salt evaporation ponds, and contains a high concentration of an amphoteric substance such as betaine which is in response to salt stress.

Excellent nutritional properties have been reported because it is known that glasswort has a dietary fiber content of 60.6% or more, 50% of total fatty acids are linolenic acid, and 40% or more of total amino acids are essential amino acids. Meanwhile, glasswort has been used as a therapeutic agent for constipation, dyspepsia, hepatitis, and kidney disease in the Korean traditional medicine and private sectors. Various useful physiological activities of glasswort have been reported, and anti-oxidation, anti-fatigue, anti-inflammation, thrombogenesis inhibition and thrombolysis activities, immunocompetence enhancement, and the like have been reported.

When porous silica impregnated with an agar and glasswort extract as described above is included in a first fertilizer composition, active ingredients included in the agar and glasswort extract may be provided during the growth of *Cannabis sativa* L., thereby increasing the growth efficiency. In particular, the growth of female plants may be promoted, so that it is possible to improve the seed and fruit harvest efficiency of *cannabis* female plants to much higher levels.

In the agar extract, a ground product obtained by grinding dried agar may be eluted by using a polar solvent such as water and a $C_1$ to $C_6$ alcohol such as ethanol and methanol, or a mixed solvent having a mixture ratio of alcohol to water of 1:0.1 to 1:10, and more specifically, water may be used as an extraction solvent. In this case, the agar extract may be an extract extracted at an extraction temperature of 10° C. to 100° C., preferably, room temperature.

The extraction solvent may be used at 2 to 50 times, preferably, 2 to 20 times based on the weight of a sample. For extraction, the sample may be left to stand in an extraction solvent for 1 to 72 hours, specifically for 1 to 24 hours for percolation.

The agar extract may be a product obtained by concentrating a filtered extract under reduced pressure by a vacuum rotary concentrator, and is not limited as long as the agar extract is an agar extract which may exhibit an anti-obesity effect of the present invention, and the agar extract includes all of a liquid extract, a diluted or concentrated liquid of the liquid extract, a dried product obtained by drying the liquid extract, or a crude purified extract or a purified extract thereof.

The glasswort extract may also be produced using the same method as in the agar extract.

Porous silica is impregnated with a mixed liquid obtained by mixing the agar extract and the glasswort extract at a weight ratio of 1:1 to adsorb the natural extract onto the porous silica.

The adsorbed natural extract is continuously released in the soil for a long period of time, so that it is possible to exhibit the effect of using a fertilizer for a long period of time even by using a method of spraying a fertilizer composition once without any need to administer the fertilizer composition repeatedly.

*Cannabis sativa* L. was grown by sowing *Cannabis sativa* L. seeds, and for the sowing of *Cannabis sativa* L. seeds, 4 to 5 seeds were each hill-seeded at an interval of 30 to 50 cm.

When *Cannabis sativa* L. seeds were sown by hill seeding as described above, and then *Cannabis sativa* L. is germinated, light may be provided under a photosynthetic photon flux density (PPFD) condition of 15 to 20 $\mu Mm^{-2}s^{-1}$ for more specifically 15 to 30 days in order to induce the growth, and then light may be provided under a photosynthetic photon flux density (PPFD) condition of 30 to 40 $\mu Mm^{-2}s^{-1}$ for 15 to 30 days.

When the growth of *Cannabis sativa* L. is induced under the light providing condition as described above, *Cannabis sativa* L. forms budding flowers, and the difference in shape of budding flowers makes it possible to distinguish between male budding flowers and female budding flowers.

At the time point when it was possible to distinguish between the male budding flowers and the female budding flowers, the *Cannabis sativa* L. where the male budding flowers were formed was all removed, only the *Cannabis sativa* L. where the female budding flowers were formed was left, and then the cultivation was performed.

Thereafter, light is provided under a photosynthetic photon flux density (PPFD) condition of 30 to 40 $\mu Mm^{-2}s^{-1}$ for 5 hours to 16 hours daily for 15 to 30 days.

More specifically, light is provided under a photosynthetic photon flux density (PPFD) condition of 40 $\mu Mm^{-2}s^{-1}$ for 10 hours to 12 hours.

As described above, when light is provided under a high light condition by increasing the lighting condition, *Cannabis sativa* L. promotes the vegetative growth.

That is, when light is provided under a low light condition as described above, flower buds are formed and budding flowers are formed rapidly through reproductive growth.

Thereafter, it is possible to produce desired *Cannabis sativa* L. seeds by performing a vegetative growth under a high light condition.

In this case, the *Cannabis sativa* L. where female budding flowers are formed may be referred to as a *cannabis* female plant. As previously described, *Cannabis sativa* L. is a plant corresponding to dioecism, and it is possible to differentiate from male plants and female plants according to the type of budding flower.

After *Cannabis sativa* L. where male budding flowers were formed was all removed, the formation of male flowers was induced in *cannabis* female plants by spraying a second fertilizer composition on *Cannabis sativa* L. where female budding flowers were formed.

More specifically, in *cannabis* female plants, female flowers are generally formed and bloom, but *Cannabis sativa* L. simultaneously includes characteristics of monoecism, and thus is affected by growth conditions, thereby enabling male flowers to be formed in *cannabis* female plants.

By using this point, it is attempted to spray a fertilizer composition on *cannabis* female plants and promote the vegetative growth and simultaneously induce the formation of male flowers.

As the second fertilizer composition, it is possible to use a mixture of a nitrogen fertilizer, a phosphate fertilizer, a potassium fertilizer, and porous silica.

As the second fertilizer composition, it is possible to use a mixed fertilizer obtained by mixing 30 to 50 parts by weight of the phosphate fertilizer, 30 to 50 parts by weight of the potassium fertilizer, and 40 to 60 parts by weight of porous silica based on 100 parts by weight of the nitrogen fertilizer.

The ingredients and contents of the second fertilizer composition are the same as those of the first fertilizer composition previously described, but the porous silica is not impregnated with a natural extract, but is impregnated with a mixture of aminoethoxyvinyl glycine (AVG), α-aminoisobutyric acid (AIB), and an aqueous silver chloride (AgCl) solution, unlike the first fertilizer composition.

The mixture may exhibit an effect as an ethylene inhibitor, and more preferably, is characterized by using an ethylene inhibitor including 30 to 50 parts by weight of aminoethoxyvinyl glycine (AVG), 30 to 50 parts by weight of α-aminoisobutyric acid (AIB), 10 to 15 parts by weight of an aqueous silver chloride (AgCl) solution, and 5 to 10 parts by weight of a surfactant based on 100 parts by weight of a solvent. When the mixture is used within the above range, an effect of inhibiting a plant hormone ethylene is increased due to the interaction between the ingredients within the mixing range, thereby enabling male flowers to be formed in female plants.

The solvent and the surfactant are ethanol and Tween 80, respectively, but are not limited to the examples, and ingredients usable as the solvent and the surfactant can be used without limitation.

Porous silica powder particles may be impregnated with the mixture by immersing porous silica powder in the mixture, and thereafter, the impregnated mixture may be released into the soil through porous silica particles for a long period of time.

In order to enhance the effect as the ethylene inhibitor, the formation of male flowers may be induced by a method of spraying the aforementioned mixture on *Cannabis sativa* L. where female budding flowers are formed, but when the method as described above is used, there occurs a problem in that the work efficiency deteriorates as compared to the case where the mixture is provided as a fertilizer composition as in the present invention because the formation of male flowers need to be induced by spraying the ethylene inhibitor directly on *Cannabis sativa* L.

When the mixture is provided only as the ethylene inhibitor, the mixture does not affect greatly the growth of *Cannabis sativa* L., but when the mixture is provided as a fertilizer composition as in the present invention, the mixture may affect the growth of *Cannabis sativa* L., and in addition, *Cannabis sativa* L. is naturally exposed to the ethylene inhibitor for a long period of time, so that it is possible to exhibit a more advantageous effect on the formation of male flowers.

That is, when a limited space such as a glass greenhouse or a plastic greenhouse is used during the cultivation of *Cannabis sativa* L., it is not possible to show a big difference in terms of efficiency even though the formation of male flowers is induced by using the method of spraying an ethylene inhibitor, but when *Cannabis sativa* L. is cultivated in an unlimited space, there may occur a problem in that the ethylene inhibitor is washed away or is not efficiently sprayed on *Cannabis sativa* L. by rainwater when the method of spraying an ethylene inhibitor is used.

Thus, when a second fertilizer composition is used as in the present invention, it can be said that it is possible to efficiently form male flowers in *Cannabis sativa* L. without any limitation of space.

In general, male flowers of *Cannabis sativa* L. has a problem in that natural fertilization is impossible because the flowering period in male flowers is delayed by about 25 days as compared to that in female flowers.

In the case of the United States, in order to prevent these problems, pollen of male flowers is separately collected and stored, fertilization from the pollen is induced in female flowers using a brush, and then seeds are yielded and collected.

This reflects the fact that natural fertilization is impossible because *cannabis* male flowers generally have a flowering period later than that of female flowers.

It is common for *Cannabis sativa* L. to be fertilized by blowing pollen by wind and delivering pollen of male flowers to female flowers.

Thus, in order to produce *Cannabis sativa* L. seeds, as in the United States, it is possible to use a method of collecting pollen of male flowers and artificially inducing the fertilization in female flowers by using the pollen, or a method of advancing the flowering period of male flowers and making the flowering period of male flowers coincide with that of female flowers, and then inducing the natural fertilization.

When the second fertilizer composition is used as in the present invention, male flowers are formed in female plants by an ethylene inhibitor in the soil during the growth of *cannabis*, and male flowers formed in female plants enable natural fertilization by coinciding with the flowering period of female flowers.

For the natural fertilization of pollen of male flowers with female flowers, a glass or plastic greenhouse may be equipped with a large electric fan or fans, so that the wind may move pollen of male flowers, the pollen is delivered to female flowers, and as a result, natural fertilization may occur.

Apart from using the fertilizer composition as described above, if necessary, a vegetative growth may be performed under the high light condition for 30 days, and it is possible to treat a shoot apex of the *Cannabis sativa* L. where the male budding flowers are formed with an ethylene inhibitor.

When the shoot apex of the *Cannabis sativa* L. where the female budding flowers are formed is treated with an ethylene inhibitor as in the present invention, male flowers are formed in female plants by the ethylene inhibitor, and the flowering period of the male flowers formed in female plants coincides with the flowering period of female flowers, thereby making natural fertilization possible.

Even when an ethylene inhibitor is sprayed on the shoot apex in the same manner as in the case of using a fertilizer composition, it is possible to form male flowers in female plants, and the flowering period of male flowers coincides with that of female flowers, thereby making natural fertilization possible.

In the case of dioecious plants, the plant hormone ethylene acts on the formation of female flowers and male flowers. In female plants, the amount of plant hormone ethylene produced is large, so that female flowers are formed, and in the case of in male plants, the amount of plant hormone ethylene produced is small, so that male flowers are formed.

Typically, it is known that when female plants are treated with cobalt or silver ions, the formation of male flowers may be induced by suppressing the production of ethylene.

However, during the treatment with cobalt and silver ions, treatment with a large amount of cobalt and silver ions is needed in order to suppress the production of ethylene, and in this case, a material such as silver thiosulfate (STS) is used, and as a result, there is a problem which may cause an environmental problem, and the like.

Recently, STS is an environmental pollutant and corresponds to a material whose use has been prohibited.

Thus, in the present invention, it is possible to use, as the ethylene inhibitor, a material selected from the group consisting of aminoethoxyvinyl glycine (AVG), α-aminoisobutyric acid (AIB), an aqueous silver nitrate ($AgNO_3$) solution, an aqueous silver chloride (AgCl) solution, and a mixture thereof.

Preferably, it is intended to exhibit the use as an effective ethylene inhibitor by using a mixture of aminoethoxyvinyl glycine (AVG), α-aminoisobutyric acid (AIB), and an aqueous silver chloride (AgCl) solution.

More preferably, it is characterized by using an ethylene inhibitor including 30 to 50 parts by weight of aminoethoxyvinyl glycine (AVG), 30 to 50 parts by weight of α-aminoisobutyric acid (AIB), 10 to 15 parts by weight of an aqueous silver chloride (AgCl) solution, and 5 to 10 parts by weight of a surfactant based on 100 parts by weight of a solvent. When the mixture is used within the above range, an effect of inhibiting a plant hormone ethylene is increased due to the interaction between the ingredients within the mixing range, thereby enabling male flowers to be formed in female plants.

The solvent and the surfactant are ethanol and Tween 80, respectively, but are not limited to the examples, and ingredients usable as the solvent and the surfactant can be used without limitation.

Treatment of a shoot apex of the *Cannabis sativa* L. where the female budding flowers are formed with an ethylene inhibitor causes sex conversion, thereby forming male flowers in female plants.

Thereafter, light is provided under a photosynthetic photon flux density (PPFD) condition of 10 $\mu Mm^{-2}s^{-1}$ for 10 hours to 12 hours daily in order to promote the induction of male flower formation.

In general, the vegetative growth and reproductive growth of *Cannabis sativa* L. are promoted under a long-day condition and a short-day condition.

More specifically, vegetative growth allows *Cannabis sativa* L. to be grown by providing light under a long-day condition for approximately 16 hours daily, and reproductive grow allows *Cannabis sativa* L. to be grown by providing light under a short-day condition within 12 hours daily.

The present invention enables desired *Cannabis sativa* L. seeds to be produced by adjusting the intensity of light without inducing vegetative growth and reproductive growth under these long-day and short-day conditions to promote vegetative growth or promote reproductive growth.

For *Cannabis sativa* L. germinated by sowing *Cannabis sativa* L. seeds, light is primarily provided under a photosynthetic photon flux density (PPFD) condition of 20 $\mu Mm^{-2}s^{-1}$ for 10 hours to 12 hours daily for 30 days, and light is secondarily provided under a photosynthetic photon flux density (PPFD) condition of 40 $\mu Mm^{-2}s^{-1}$ for 10 hours to 12 hours daily for 30 days.

Actually, *Cannabis sativa* L. is grown under a short-day condition, but as the intensity of light is regulated, the adjustment of the intensity of light enables vegetative growth to be equal to or more than the growth of *Cannabis sativa* L. under a long-day condition.

For typical growth of *Cannabis sativa* L., budding flowers are formed only when *Cannabis sativa* L. is subjected to vegetative growth under a long-day condition of two months or more, and then flowers bloom and are fertilized only when reproductive growth is induced under a short-day condition.

After a sufficient vegetative growth period, a natural fertilization process may be performed only when reproductive growth is induced.

Focusing on the fact that the cultivation condition of *Cannabis sativa* L. is performed in a glass greenhouse or plastic greenhouse, *Cannabis sativa* L. seeds were produced by varying the intensity of light in order to obtain *Cannabis sativa* L. seeds by sowing *Cannabis sativa* L. seeds regardless of a typical cultivation period of *Cannabis sativa* L.

As described above, even though the time when light is provided is not a long-day condition, but a short-day condition, an efficient vegetative growth of *Cannabis sativa* L. is performed when light is provided by varying the intensity of light at an interval of 30 days, and as a result, budding flowers are formed.

Through budding flowers, *Cannabis sativa* L. can be distinguished as a female plant or a male plant. In order to use the *Cannabis sativa* L. for fiber, *Cannabis sativa* L. is typically grown to a height of more than 1.5 m and used, but in the present invention, *Cannabis sativa* L. was treated with an ethylene inhibitor when *Cannabis sativa* L. was grown to a height of approximately 1 m by performing vegetative growth under the above condition considering that *Cannabis sativa* L. was produced for obtaining the CBD.

Thereafter, reproductive growth was induced by again providing the degree of irradiation of light under a photosynthetic photon flux density (PPFD) condition of 10 $\mu Mm^{-2}s^{-1}$ for 10 to 12 hours daily.

When the reproductive growth is induced as described above, male flowers bloom in female plants where sex conversion occurs, and it is possible to produce *Cannabis sativa* L. seeds by natural fertilization of the male flowers with female flowers blooming in female plants where sex conversion does not occur.

For the natural fertilization of pollen of male flowers with female flowers, a glass or plastic greenhouse may be equipped with a large electric fan or fans, so that the wind may move pollen of male flowers, the pollen is delivered to female flowers, and as a result, natural fertilization may occur.

The thus obtained *Cannabis sativa* L. seeds are germinated and cultivated as *cannabis* female plants, and the *cannabis* female plants typically allow only female flowers to bloom when female plants are not treated with an ethylene inhibitor.

The thus produced female flowers are collected without damage and used for the production of an *cannabis* extract, tetrahydrocannabinol (THC) is included in an amount of 0.5 wt % or less in the *cannabis* extract, and cannabidiol (CBD) is included in an amount of 0.5 wt % or more, leading to the use as a pharmaceutical composition or food composition.

According to the method for producing *Cannabis sativa* L. seed of the present invention, when *Cannabis sativa* L. seeds are used by a method for producing *Cannabis sativa* L. seeds for efficiently cultivating a low-narcotic *cannabis* variety, it is possible to cultivate *cannabis* female plants where female flowers are formed, and it is possible to improve the quantity of *cannabis* female flowers.

DETAILED DESCRIPTION

Hereinafter, the Examples of the present invention will be described in detail such that a person skilled in the art to which the present invention pertains can easily carry out the present invention. However, the present invention can be implemented in various different forms, and is not limited to the Examples described herein.

Production of *Cannabis sativa* L. Seeds Using Fertilizer Composition

Production of *Cannabis sativa* L. Seeds

*Cannabis sativa* L. seeds were produced using an IH3 variety known as a low-narcotic variety.

*Cannabis sativa* L. seeds were sown and cultivated in a glass greenhouse around March. *Cannabis sativa* L. seeds were sown at an interval of 50 cm in the glass greenhouse. Before sowing, a first fertilizer composition was sprayed on the soil, the soil was tilled and prepared, and then 4 to 5 seeds were each hill-seeded. After sowing, when *Cannabis sativa* L. was germinated, all seedlings were thinned out while only one healthy seedling was retained.

When seeds were sown and *Cannabis sativa* L. germinated, light was provided under a photosynthetic photon flux density (PPFD) condition of 20 $\mu Mm^{-2}s^{-1}$ for 10 hours to 12 hours daily.

When *cannabis* flower buds were formed, male plants were all removed and all thinned out while retaining only female plants.

Thereafter, the formation of male flowers in *cannabis* female plants was induced by spraying a second fertilizer composition. Even after the second fertilizer composition was sprayed, the condition under which light was provided was maintained in the same manner as described above.

When it was confirmed that male budding flowers were formed in the *cannabis* female plant and male flowers were blooming, natural fertilization was induced by operating a large electric fan in the glass greenhouse to blow pollen of male flowers by wind.

After the natural fertilization was sufficiently induced, seeds could be confirmed by the unaided eye. When the seeds were sufficiently browned and could be collected, the seeds were collected, and then dried. Thereafter, *Cannabis sativa* L. seeds were produced by shaking out and harvesting seeds.

Difference in growth of *Cannabis sativa* L. according to difference in first fertilizer composition 1. Preparation of Agar Extract After an extraction solvent distilled water was added to an agar (*Gelidium amansii*) extract sample at a ratio of 1:10 (w:v) and then the agar extract sample was completely immersed, extraction was performed repeatedly three times at 80° C. under reflux for each 3 hours. The liquid extract was filtered with a Whatman No. 2 filter paper. A powder sample was prepared by concentrating the filtrate at 60° C. under reduced pressure and used for the experiment.

2. Preparation of Glasswort Extract

A glasswort extract was prepared using the same method as in the agar extract.

3. Preparation of Fine Powder Silica

A fine powder silica was prepared so as to have an average particle diameter of 5 to 10 µm by grinding silica, and was immersed in a mixed extract in which the agar extract and the glasswort extract were mixed at a weight ratio of 1:1 to immerse the mixed extract in the fine powder silica.

4. Preparation of Fertilizer Composition

A fertilizer composition was prepared by mixing 50 parts by weight of a phosphate fertilizer, 50 parts by weight of a potassium fertilizer, and 60 parts by weight of fine powder silica with 100 parts by weight of a nitrogen fertilizer.

5. Difference in Growth of *Cannabis sativa* L. According to Use of Fertilizer Composition The differences in growth of *Cannabis sativa* L. were compared using *Cannabis sativa* L. seeds in which only female plants collected in the previous experiment were cultivated.

Before sowing *Cannabis sativa* L. seeds,
i) 10 kg of the fertilizer composition was sprayed, the soil was tilled and prepared, and then *Cannabis sativa* L. seeds were sown
ii) for comparison, 10 kg of the nitrogen fertilizer was sprayed, the soil was tilled and prepared, and then *Cannabis sativa* L. seeds were sown
iii) for comparison, 10 kg of a fertilizer composition obtained by removing only fine powder silica from the above fertilizer composition was sprayed, the soil was tilled and prepared, and then *Cannabis sativa* L. seeds were sown After the *Cannabis sativa* L. seeds were sown under the conditions of i) to iii), the differences in growth were compared by measuring the lengths of *Cannabis sativa* L. under the same growth conditions.

After the *Cannabis sativa* L. was cultivated for approximately 2 months, the lengths of the *Cannabis sativa* L. were compared. For confirmation of sample sizes, 10 seedlings of *Cannabis sativa* L. were each used, and the lengths of *Cannabis sativa* L. were measured on average.

According to the measurement result, in the case of i) fertilizer, it was confirmed that the average length of the *Cannabis sativa* L. was 1.7 m, and in the case of ii) fertilizer, the average length of the *Cannabis sativa* L. was approximately 1.2 m, and in the case of iii) fertilizer, it was confirmed that the average length of the *Cannabis sativa* L. was 1.3 m.

It was confirmed that substantially the same degree of growth of *Cannabis sativa* L. was confirmed except for i) fertilizer, and i) fertilizer promoted the growth of *Cannabis sativa* L., so that a better degree of growth of *Cannabis sativa* L. could be confirmed.

Preparation of Second Fertilizer Composition

Ethanol, AVG, AIB, an aqueous silver chloride (AgCl) solution, and Tween 80 were mixed and stirred so as to be uniformly mixed using a stirrer, and then the resulting mixture was prepared as an ethylene inhibitor.

TABLE 1

|  | ES1 | ES2 | ES3 | ES4 | ES5 |
| --- | --- | --- | --- | --- | --- |
| Ethanol | 100 | 100 | 100 | 100 | 100 |
| AVG | 20 | 30 | 40 | 50 | 60 |
| AIB | 20 | 30 | 40 | 50 | 60 |
| AgCl | 5 | 10 | 12 | 15 | 20 |
| Tween 80 | 10 | 10 | 10 | 10 | 10 |

(Unit parts by weight)

Porous silica powder was immersed in ES1 to ES5, the porous silica powder particles were sufficiently impregnated with ES1 to ES5, respectively, and then 50 parts by weight of a phosphate fertilizer, 50 parts by weight of a potassium fertilizer, and 60 parts by weight of fine powder silica were mixed with 100 parts by weight of a nitrogen fertilizer, thereby preparing a second fertilizer composition.

Evaluation of Formation of Male Flowers

The second fertilizer composition for ES1 to ES5 was sprayed on *cannabis* female plants in each section, and it was confirmed whether male flowers were formed.

It was confirmed by the unaided eye whether male budding flowers were formed. Considering that a plurality of budding flowers was formed at one *cannabis* plant, the number of male budding flowers was confirmed, a case where 0 and less than 5 male budding flowers were formed, a case where 5 to 10 male budding flowers were confirmed, and a case where more than 10 male budding flowers were formed were marked with X, Δ, and ○, respectively. The results are shown in the following Table 2.

TABLE 2

|  | ES1 | ES2 | ES3 | ES4 | ES5 |
| --- | --- | --- | --- | --- | --- |
| Formation of male budding flowers | X | Δ | ○ | ○ | Δ |

As shown in Table 2, it was confirmed that the difference in formation of male budding flowers was exhibited according to the difference in content of the ingredient of the second fertilizer composition. In the case of ES1, the effect by the ethylene inhibitor was insignificant, so that it could be confirmed that sex conversion rarely occurred, and in the case of ES2 and ES5, sex conversion occurred, but the degree of conversion was insignificant as compared to other ethylene inhibitors, so that there was a problem in that it was difficult to produce *Cannabis sativa* L. seeds by natural fertilization.

Production of *Cannabis sativa* L. Seeds According to Light Conditions and Treatment with Ethylene Inhibitor Production of *Cannabis sativa* L. Seeds

*Cannabis sativa* L. seeds were produced using an IH3 variety known as a low-narcotic variety.

*Cannabis sativa* L. seeds were sown and cultivated in a glass greenhouse around March. *Cannabis sativa* L. seeds were sown at an interval of 50 cm in the glass greenhouse. Before sowing, a fertilizer composition was sprayed on the soil, the soil was tilled and prepared, and then 4 to 5 seeds were each hill-seeded. After sowing, when *Cannabis sativa* L. was germinated, all seedlings were thinned out while only one healthy seedling was retained.

When seeds were sown and *Cannabis sativa* L. was germinated, light was provided under the same condition as a photosynthetic photon flux density (PPFD) condition of 20 $\mu Mm^{-2}s^{-1}$ for 10 hours to 12 hours daily for approximately 30 days. When *cannabis* flower buds were formed, male plants were all removed, only female plants were retained, and then light was provided under a PPFD condition of 40 $\mu Mm^{-2}s^{-1}$ for 10 hours to 12 hours daily for 30 days.

Thereafter, the ethylene inhibitor prepared under the same condition as that in the following Table 1 was sprayed on the shoot apex of a *cannabis* female plant.

After the ethylene inhibitor was sprayed, light was provided under a PPFD condition of 10 $\mu Mm^{-2}s^{-1}$ for 10 hours to 12 hours.

When it was confirmed that male budding flowers were formed in the *cannabis* female plant on which the ethylene inhibitor was sprayed and male flowers were blooming, natural fertilization was induced by operating a large electric fan in the glass greenhouse to blow pollen of male flowers by wind.

After the natural fertilization was sufficiently induced, seeds could be confirmed by the unaided eye. When the seeds were sufficiently browned and could be collected, the seeds were collected, and then dried. Thereafter, *Cannabis sativa* L. seeds were produced by shaking out and harvesting seeds.

Preparation of Ethylene Inhibitor

Ethanol, AVG, AIB, an aqueous silver chloride (AgCl) solution, and Tween 80 were mixed and stirred so as to be uniformly mixed using a stirrer, and then the resulting mixture was prepared as an ethylene inhibitor.

TABLE 3

|  | EE1 | EE2 | EE3 | EE4 | EE5 |
|---|---|---|---|---|---|
| Ethanol | 100 | 100 | 100 | 100 | 100 |
| AVG | 20 | 30 | 40 | 50 | 60 |
| AIB | 20 | 30 | 40 | 50 | 60 |
| AgCl | 5 | 10 | 12 | 15 | 20 |
| Tween 80 | 10 | 10 | 10 | 10 | 10 |

(Unit parts by weight)

Evaluation of Formation of Male Flowers

After the ethylene inhibitor for EE1 to EE5 was each sprayed on 5 seedlings of *cannabis* female plants, it was confirmed whether male flowers were formed.

It was confirmed by the unaided eye whether male budding flowers were formed. Considering that a plurality of budding flowers was formed at one *cannabis* plant, the number of male budding flowers was confirmed, a case where 0 and less than 5 male budding flowers were formed, a case where 5 to 10 male budding flowers were confirmed, and a case where more than 10 male budding flowers were formed were marked with X, Δ, and ○, respectively. The results are shown in the following Table 4.

TABLE 4

|  | EE1 | EE2 | EE3 | EE4 | EE5 |
|---|---|---|---|---|---|
| Formation of male budding flowers | X | ○ | ○ | ○ | Δ |

As shown in Table 4, it was confirmed that the difference in formation of male budding flowers was exhibited according to the difference in content of the ingredient of the ethylene inhibitor. In the case of EE1, the effect by the ethylene inhibitor was insignificant, so that it could be confirmed that sex conversion rarely occurred, and in the case of EE5, sex conversion occurred, but the degree of conversion was insignificant as compared to other ethylene inhibitors, so that there was a problem in that it was difficult to produce *Cannabis sativa* L. seeds by natural fertilization.

Difference in Flowering Period Lengths of Female and Male Flowers According to Light Condition In order to confirm effect of light on the growth of *Cannabis sativa* L., the lighting conditions were varied, and then the flowering time point of female plants and the flowing time point of male flowers were confirmed, and the difference in flowering periods of female flowers and male flowers was confirmed. During the growth of *Cannabis sativa* L., the lighting was provided in the same manner as above for 10 to 12 hours daily.

The lighting conditions are shown in the following Table 5.

TABLE 5

|  | 30 days after germination | 30 days later | After treatment with ethylene inhibitor | Difference in flowering periods (day) |
|---|---|---|---|---|
| PE1 | 20 $\mu Mm^{-2}s^{-1}$ PPFD | 40 $\mu Mm^{-2}s^{-1}$ PPFD | 10 $\mu Mm^{-2}s^{-1}$ PPFD | 1 |
| PE2 | 20 $\mu Mm^{-2}s^{-1}$ PPFD | 20 $\mu Mm^{-2}s^{-1}$ PPFD | 20 $\mu Mm^{-2}s^{-1}$ PPFD | 16 |
| PE3 | 40 $\mu Mm^{-2}s^{-1}$ PPFD | 40 $\mu Mm^{-2}s^{-1}$ PPFD | 40 $\mu Mm^{-2}s^{-1}$ PPFD | 20 |
| PE4 | 10 $\mu Mm^{-2}s^{-1}$ PPFD | 10 $\mu Mm^{-2}s^{-1}$ PPFD | 10 $\mu Mm^{-2}s^{-1}$ PPFD | 15 |

As shown in Table 5, it was confirmed that according to the difference in lighting conditions, the difference in flowering periods of female flowers and male flowers was exhibited. When the difference in flowering periods is exhibited to be 2 weeks or more, the natural fertilization is impossible, so that it can be said that production of *Cannabis sativa* L. is greatly affected because the artificial fertilization needs to be performed manually by humans.

Difference in Growth of *Cannabis sativa* L. According to the Difference in Fertilizers 1. Production of Agar Extract After an extraction solvent distilled water was added to an agar (*Gelidium amansii*) extract sample at a ratio of 1:10 (w:v) and then the agar extract sample was completely immersed, extraction was performed repeatedly three times at 80° C. under reflux for each 3 hours. The liquid extract was filtered with a Whatman No. 2 filter paper. A powder sample was prepared by concentrating the filtrate at 60° C. under reduced pressure and used for the experiment.

2. Preparation of Glasswort Extract

A glasswort extract was prepared using the same method as in the agar extract.

3. Preparation of Fine Powder Silica

A fine powder silica was prepared so as to have an average particle diameter of 5 to 10 µm by grinding silica, and was immersed in a mixed extract in which the agar extract and the glasswort extract were mixed at a weight ratio of 1:1 to immerse the mixed extract in the fine powder silica.

4. Preparation of Fertilizer Composition

A fertilizer composition was prepared by mixing 50 parts by weight of a phosphate fertilizer, 50 parts by weight of a potassium fertilizer, and 60 parts by weight of fine powder silica with 100 parts by weight of a nitrogen fertilizer.

5. Difference in Growth of Cannabis sativa L. According to Use of Fertilizer Composition The differences in growth of Cannabis sativa L. were compared using Cannabis sativa L. seeds in which only female plants collected in the previous experiment were cultivated.

Before sowing Cannabis sativa L. seeds, i) 10 kg of the fertilizer composition was sprayed, the soil was tilled and prepared, and then Cannabis sativa L. seeds were sown;

ii) for comparison, 10 kg of the nitrogen fertilizer was sprayed, the soil was tilled and prepared, and then Cannabis sativa L. seeds were sown; and iii) for comparison, 10 kg of a fertilizer composition obtained by removing only fine powder silica from the above fertilizer composition was sprayed, the soil was tilled and prepared, and then Cannabis sativa L. seeds were sown.

After the Cannabis sativa L. seeds were sown under the conditions of i) to iii), the differences in growth were compared by measuring the lengths of Cannabis sativa L. under the same growth conditions.

After the Cannabis sativa L. was cultivated for approximately 2 months, the lengths of the Cannabis sativa L. were compared. For confirmation of sample sizes, 10 seedlings of Cannabis sativa L. were each used, and the lengths of Cannabis sativa L. were measured on average.

According to the measurement result, in the case of i) fertilizer, it was confirmed that the average length of the Cannabis sativa L. was 1.7 m, and in the case of ii) fertilizer, the average length of the Cannabis sativa L. was approximately 1.2 m, and in the case of iii) fertilizer, it was confirmed that the average length of the Cannabis sativa L. was 1.3 m.

It was confirmed that substantially the same degree of growth of Cannabis sativa L. was exhibited except for i) fertilizer, and i) fertilizer promoted the growth of Cannabis sativa L., so that a better degree of growth of Cannabis sativa L. could be confirmed.

Although preferred Examples of the present invention have been described in detail hereinabove, the right scope of the present invention is not limited thereto, and it should be understood that many variations and modifications of those skilled in the art using the basic concept of the present invention, which is defined in the following claims, will also fall within the right scope of the present invention.

What is claimed is:

1. A method for producing Cannabis sativa L. seed capable of cultivating Cannabis female plants, the method comprising:

spraying a first fertilizer composition on soil before sowing Cannabis sativa L. seeds;

sowing Cannabis sativa L. seeds after tilling and preparing the soil on which the first fertilizer composition is sprayed;

inducing the formation of budding flowers by providing Cannabis sativa L. germinated from the Cannabis sativa L. seeds with light, wherein the light is provided under a photosynthetic photon flux density (PPFD) condition of 15 to 20 $\mu Mm^{-2}s^{-1}$ for 5 to 16 hours for 15 to 30 days: and then providing light under a photosynthetic photon flux density (PFFD) condition of 30 to 40 $\mu Mm^{-2}s^{-1}$ for 5 to 16 hours for 15 to 30 days;

inducing the formation of male budding flowers in Cannabis female plants by removing all Cannabis sativa L. male plants and retaining female plants where male budding flowers are formed by spraying a second fertilizer composition on Cannabis sativa L. female plants;

after the second fertilizer composition was sprayed the light is provided under a photosynthetic photon flux density (PPFD) condition of 10 $\mu Mm^{-2}s^{-1}$ for 10 to 12 hours and;

producing seeds by fertilizing pollen in the male budding flowers formed in the Cannabis female plants with female flowers.

2. The method of claim 1, wherein the first fertilizer composition comprises a nitrogen fertilizer, a phosphate fertilizer, a potassium fertilizer, and porous silica.

3. The method of claim 1, wherein the second fertilizer composition comprises a nitrogen fertilizer, a phosphate fertilizer, a potassium fertilizer, and porous silica, and the porous silica is a product in which a mixture of solvent, surfactant aminoethoxyvinyl glycine (AVG), α-aminoisobutyric acid (AIB), and an aqueous silver chloride (AgCl) solution is adsorbed.

4. The method of claim 1, wherein the female flowers are used as a Cannabis extract by harvesting flowers and flower petals, and the Cannabis extract is low narcotic.

5. The method of claim 4, wherein the low narcotic comprises tetrahydrocannabinol (THC) in an amount of 0.5 wt % or less in the ingredients of the total extract.

6. The method of claim 4, wherein the low narcotic comprises cannabidiol (CBD) in an amount of 0.5 wt % or more in the ingredients of the total extract.

* * * * *